US007102026B2

(12) United States Patent
Dolitzky et al.

(10) Patent No.: US 7,102,026 B2
(45) Date of Patent: *Sep. 5, 2006

(54) **PROCESS FOR PREPARING AND ISOLATING *RAC*-BICALUTAMIDE AND ITS INTERMEDIATES**

(75) Inventors: Ben-Zion Dolitzky, Petach Tiqva (IL); Ofer Reany, Lower Galilee (IL); Jenny Shammai, Kiryat Yam (IL)

(73) Assignee: TEVA Gyógyszergyár Zártkörüen Müködö Részvénytársaság, Debrecen (HU)

( * ) Notice: Subject to any disclaimer, the term of this patent is extended or adjusted under 35 U.S.C. 154(b) by 0 days.

This patent is subject to a terminal disclaimer.

(21) Appl. No.: 10/606,403

(22) Filed: Jun. 25, 2003

(65) Prior Publication Data

US 2004/0044249 A1    Mar. 4, 2004

Related U.S. Application Data

(63) Continuation-in-part of application No. 10/170,721, filed on Jun. 13, 2002, now Pat. No. 6,737,550.

(60) Provisional application No. 60/371,069, filed on Apr. 9, 2002, provisional application No. 60/298,009, filed on Jun. 13, 2001.

(51) Int. Cl.
*C07C 255/50*  (2006.01)
*A61K 31/275*  (2006.01)

(52) U.S. Cl. .................. 558/413; 514/520; 514/521; 514/523; 514/618; 564/162

(58) Field of Classification Search .............. 564/162; 514/618, 520, 521, 522; 558/413
See application file for complete search history.

(56) References Cited

U.S. PATENT DOCUMENTS

| | | | | |
|---|---|---|---|---|
| 3,254,094 | A | | 5/1966 | Ross |
| 3,875,229 | A | * | 4/1975 | Gold ........................ 564/202 |
| 4,554,381 | A | | 11/1985 | Desbois |
| 4,636,505 | A | | 1/1987 | Tucker |
| 5,300,652 | A | * | 4/1994 | Keil et al. ............... 548/375.1 |
| 5,723,485 | A | | 3/1998 | Gungor et al. |
| 6,160,011 | A | | 12/2000 | Miller et al. |
| 6,184,249 | B1 | | 2/2001 | Sovak et al. |
| 6,291,504 | B1 | | 9/2001 | Nugiel et al. |
| 6,306,874 | B1 | | 10/2001 | Fraley et al. |
| 6,358,985 | B1 | | 3/2002 | Anthony et al. |
| 6,479,692 | B1 | * | 11/2002 | Ekwuribe et al. ........... 558/413 |
| 6,797,843 | B1 | * | 9/2004 | Dolitzky et al. ............ 568/28 |
| 2003/0191337 | A1 | | 10/2003 | Shintaku et al. |

FOREIGN PATENT DOCUMENTS

| | | |
|---|---|---|
| WO | WO 93/19770 | 10/1993 |
| WO | WO 01/00608 | 1/2001 |
| WO | WO 02/24638 A1 | 3/2002 |
| WO | WO 03/097590 A1 | 11/2003 |

OTHER PUBLICATIONS

H. Tucker, et al., "Nonsteroidal Antiandrogens. Synthesis and Structure-Activity Relationships of 3-Substituted Derivatives of 2-Hydroxypropionanilides", Journal of Medicinal Chemistry, American Chemical Society. vol. 31, No. 5, May 1, 1988, pp. 954-959.
MacPeek, Donald L. et al., "Synthesis of Glycidic Esters by Epoxidation of α,β-Unsaturated Esters with Peracetic Acid," J. Am. Chem., 1959, vol. 81, pp. 680-683.
Emmons, William D. et al., "Peroxytrifluoroacetic Acid. IV. The Epoxidation of Olefins," J. Am. Chem., 1955, vol. 77, pp. 89-92.
Ho, Winston et al., "Alkylglycidic Acids: Potential New Hypoglycemic Agents," J. Med. Chem., 1986, vol. 29, pp. 2184-2190.
Lieberman, Herbert A. et al., *Pharmaceutical Dosage Forms: Tablets*, vol. 2, 2nd Ed., Marcel Dekker, Inc., New York (1990), pp. 107-200.
Database CAPLUS on STN, Chemical Abstracts, CA: 129:244921, Freskos et al., "Preparation of aromatic sulfonyl alpha-hydroxy hydroxamic acid compounds as matrix metalloprotease inhibitors".
Database CAPLUS on STN, Chemical Abstracts, CA:128:75188, Takahashi et al., "Preparation and formulation of aryl sulfides, sulfoxides, and sulfones as matrix metalloproteinase inhibitors".
Database CAPLUS on STN, Chemical Abstracts, CA: 136:12767, Slusarek et al., "Color photographic thermally processable film comprising blocked developer compound".
Database CAPLUS on STN, Chemical Abstracts, CA: 86:171116, Buettner et al., "Trifluoromethyl-substituted aminobenzonitriles".
Database CAPLUS on STN, Chemical Abstracts, CA: 108:150026, Tucker et al., "Resolution of the non-steriodal antiandrogen 4'-cyano-3-(4-fluorophenylsulfonyl)-2-hydroxy-2-methyl-3'-(trifluoromethyl) propionanilide and the determination of the absolute configuration of the active enantiomer".
Database CAPLUS on STN, Chemical Abstracts, CA: 2002:414656, James et al., "A two-step synthesis of the anti-cancer drug (r,S)-bicalutamide".
Database CAPLUS on STN, Chemical Abstracts, CA:120:191513, Horchler von Locquenghien et al., "Preparation of oxiranecarboxylates and analogs".
Database CAPLUS on STN, Chemical Abstracts, CA:89:90113, Rastetter, et al. "3,5-Dinitroperoxybenzoic acid. A crystalline, storable substitute for peroxytrifluoroacetic acid".

(Continued)

*Primary Examiner*—Shailendra Kumar
(74) *Attorney, Agent, or Firm*—Kenyon & Kenyon LLP (57) ABSTRACT

The present invention relates to a new process for the synthesis of racemic and optically active bicalutamide starting from ethyl pyruvate and methyl methacrylate. The present invention discloses processes of preparing bicalutamide intermediates including ethyl-[2-{4-fluorophenyl sulfone}]-2-hydroxy propionate, 1,2-epoxy-2-methyl propionate and 2-hydrox-2-methyl-3-(4-fluorophenylthio) propionic acid. The present invention further discloses micronized rac-bicalutamide and the preparation thereof. The present invention further discloses a new process for the isolation and purification of racemic and optically active bicalutamide.

32 Claims, 2 Drawing Sheets

OTHER PUBLICATIONS

Database CAPLUS on STN, Chemical Abstracts, CA:134:326279, Ekwuribe, et al. Asymmetric synthesis and antiandrogenic use of enantiomers of Casodex (bicalutamide) and derivatives from enantiomers of citramalic acid or proline.

* cited by examiner

Figure 1: Reaction Pathway of *rac*-Bicalutamide Synthesis Starting From Ethyl Pyruvate.

The abbreviations used are: DABCO: 1,4 diazabicyclo[2.2.2]octane; 4-FPMS: 4-fluorophenyl methyl sulfone; ACB: 5-amino-2-cyano-benzotrifluoride;THF: tetrahydrofuran; and BCL: *rac*-bicalutamide.

Figure 2: Reaction Pathway of *rac*-Bicalutamide Synthesis Starting From Methyl Methacrylate.

PROCESS FOR PREPARING AND ISOLATING RAC-BICALUTAMIDE AND ITS INTERMEDIATES

CROSS REFERENCE TO RELATED APPLICATIONS

This application is a continuation-in-part of patent application Ser. No. 10/170,721, filed Jun. 13, 2003, now U.S. Pat. No. 6,737,550 which claims the priority of provisional applications Ser. Nos. 60/298,009, filed Jun. 13, 2001 and 60/371,069, filed Apr. 9, 2002, the contents of all of which are incorporated by reference.

FIELD OF THE INVENTION

The present invention relates to a process for preparing rac-bicalutamide and its intermediates. The prevent invention also relates to micronized rac-bicalutamide and the preparation thereof. The present invention further discloses a new process for the isolation and purification of racemic and optically active bicalutamide.

BACKGROUND OF THE INVENTION

Bicalutamide is also known as N-[4-cyano-3-trifluoromethyl-phenyl]-3-[4-fluorophenyl-sulfonyl]-2-hydroxy-2-methyl-propionamide and has the following chemical formula.

Bicalutamide

Bicalutamide is an acylanilid that has anti-androgen activity. It is known to selectively decrease the testosterone level without influencing the regulation mechanisms of the hypothalamus.

The international patent No. WO 93/19770 describes both R-(−) enantiomer and S-(+) enantiomer for bicalutamide, of which the R-(−) isomer is reported to be more active and possesses lesser side-effects (e.g., headache, gynecomistia and giddiness) when used in therapy treatment.

U.S. Pat. No. 4,636,505 describes processes for preparing acylanilides.

The international patent No. WO 01/00608 describes a process for racemic and optically pure N-[4-cyano-3-trifluoromethylphenyl]-3-[4-fluorophenyl-sulfonyl]-2-hydroxy-2-methyl-propionamide. The process involves multiple steps including at least reacting with thionyl choride; hydrolyzing under aqueous basic conditions; sulfonylating with sulfonyl halogenide; and oxidizing with inorganic peroxy salt or m-chloroperbenzoic acid (MCPBA) or aqueous hydrogen peroxide. However, the synthetic pathways involve the use of substrates (such as sodium hydride) that are dangerously explosive in nature.

There is a constant need to improve the synthesis process for bicalutamide which are economical and environmental safe and feasible.

We have now found a simpler method of preparing bicalutamide and its intermediates without using dangerous oxidizing compounds such as m-chloroperbenzoic acid. In addition, the present invention also provides a novel, safe and effective method for the purification and isolation of bicalutamide.

OBJECTS AND SUMMARY OF THE INVENTION

The present invention provides new synthetic pathways for preparing rac-bicalutamide and its intermediates.

According to one object, the present invention is directed to a rac-bicalutamide intermediate having a chemical formula of [X], which represents a stable organo lithium salt of 4-fluorophenyl methyl sulfone.

According to another object, the present invention is directed to a process of preparing [X], comprising the step of reacting 4-fluorophenyl methyl sulfone with butyl lithium to form the organo lithium salt of 4-fluorophenyl methyl sulfone.

According to another object, the present invention provides a novel process for preparing rac-ethyl 1-[2-{4-fluorophenyl sulfone}]-2-hydroxy propionic acid, comprising the step of reacting the organo lithium salt of 4-fluorophenyl methyl sulfone with ethyl pyruvate.

According to another object, the present invention is directed to a rac-bicalutamide intermediate having a chemical formula of [Y], which represents a stable lithium salt of 5-amino-2-cyano-benzotrifluoride.

According to another object, the present invention provides a precess for preparing [Y], comprising the step of reacting 5-amino-2-cyano-benzotrifluoride with butyl lithium to form the lithium salt of 5-amino-cyano-benzotrifluoride.

According to another object, the present invention provides a process for preparing rac-bicalutamide, comprising the step of reacting [Y] with rac-ethyl 1-[2-{4-fluorophenyl sulfone}]-2-hydroxy propionic acid.

According to another object, the present invention provides a process for preparing rac-ethyl-[2-{4-fluorophenyl sulfone}]-2-hydroxy propionic acid, comprising the steps of:
1) mixing 4-fluorophenyl methyl sulfone with butyl lithium to obtain an intermediate having a chemical structure [X];
2) adding ethyl pyruvate; and
3) recovering rac-ethyl-[2-{4-fluorophenyl sulfone}]-2-hydroxy propionic acid.

Preferably, 1,4 diazabicyclo[2.2.2]octane in tetrahydrofuran is used as a stablizied agent in step 1.

According to another object, the present invention provides a process for preparing rac-bicalutamide comprising the steps of:
1) mixing 5-amino-2-cyano-benzotrifluoride and butyl lithium to obtain a lithium salt of 5-amino-2-cyano-benzotrifloride;
2) adding rac-ethyl-[2-{4-fluorophenyl sulfone}]-2-hydroxy propionic acid; and
3) recovering rac-bicalutamide.

Preferably, the step 1) is occurred in the presence of 1,4 diazabicyclo[2.2.2]octane in tetrahydrofuran.

According to one object, the present invention provides a novel process of preparing micronized forms of rac-bicalutamide.

According to another object, the present invention provides a synthesis process of preparing rac-bicalutamide with a particle size in which the mean particle size enhances the rate of dissolution and the reproducibility of dissolution. The present invention provides rac-bicalutamide in which the mean particle size imparts an improved and stable dissolution profile.

According to another object, the present invention provides rac-bicalutamide formulations containing rac-bicalutamide having relatively small particles, and corresponding large surface area.

According to another object, the present invention provides rac-bicalutamide with a particle size which enhances the rate of dissolution and the reproducibility of the rate of dissolution.

According to another object, the present invention provides rac-bicalutamide in which the mean particle size imparts an improved and stable dissolution profile.

According to another object, the present invention provides rac-bicalutamide and formulations containing rac-bicalutamide having a mean particle diameter of less than 200 μm.

According to another object, the present invention provides a process for preparing micronized rac-bicalutamide.

According to another object, the present invention provides pharmaceutical compositions comprising micronized rac-bicalutamide.

The present invention also provides a process for the purification and crystallization of rac-bicalutamide and its intermediates prepared by the process described above.

According to one object, the present invention provides a process for the purification and isolation of bicalutamide by solution crystallization, comprising the steps of:
(i) combining crude bicalutamide and a solvent;
(ii) crystallizing the bicalutamide from the solvent with or without seeding; and
(iii) collecting the crystals of bicalutamide.

The crude bicalutamide may or may not be substantially soluble in the solvent. Preferably the crude bicalutamide is soluble in the solvent. The resulting bicalutamide solution or suspension is crystallized by applying agitation for a time sufficient to bring about crystallization of the bicalutamide.

Preferably, in this embodiment, the solvent is selected from the group consisting of water, methanol, ethanol, DCM, toluene, PE, chloroform, hexane, 1,2-dichloroethane, diethyl ether, propanol and isopropanol.

According to another object, the present invention provides a process for the purification and isolation of bicalutamide by solution crystallization, comprising the steps of:
(i) combining crude bicalutamide and a first solvent;
(ii) adding a second solvent to the crude bicalutamide-first solvent mixture;
(iii) crystallizing the bicalutamide from the solvents; and
(iv) collecting the crystals of bicalutamide.

In one embodiment, the first solvent and the second solvent are the same. Preferably, in this embodiment, the crude bicalutamide is dissolved in an amount of first solvent sufficient to dissolve the bicalutamide. Preferably the resulting bicalutamide solution is heated to about the boiling point of the first solvent.

Preferably, in this embodiment, the amount of second solvent added to the bicalutamide solution is equal to that of the first volume. The second solvent is preferably added under reflux conditions.

Preferably the crystallizing step comprises cooling the bicalutamide solution to a temperature sufficient to bring about crystallization of bicalutamide. Most preferably the temperature sufficient to bring about crystallization of bicalutamide is about 25° C.

Preferably, in this embodiment, the first and second solvents are selected from the group consisting of ethyl acetate, acetonitrile, acetone, THF, propanol, DMF, DMSO and isobutyl methyl ketone.

In another embodiment, the present invention provides a process for the purification and isolation of bicalutamide by solution crystallization, comprising the steps of:
(i) combining crude bicalutamide and a first solvent;
(ii) adding a second solvent to the crude bicalutamide-first solvent mixture, wherein the second solvent is an anti-solvent;
(iii) crystallizing the bicalutamide from the solvents; and
(iv) collecting the crystals of bicalutamide.

Preferably, in this embodiment, the crude bicalutamide is dissolved in an amount of first solvent sufficient to dissolve the bicalutamide. Preferably the resulting bicalutamide solution is heated to about the boiling point of the first solvent. Preferably, in this embodiment, the addition of the second solvent, or anti-solvent, takes place under reflux conditions, with the second solvent being added in an amount sufficient to bring about an at least partially desolubilized bicalutamide.

Preferably, in this embodiment, following addition of the second solvent, a small volume of first solvent, sufficient to dissolve the at least partially desolubilized bicalutamide is added to the mixture.

Preferably the crystallizing step comprises cooling the bicalutamide solution to a temperature sufficient to bring about crystallization of bicalutamide. Most preferably the temperature sufficient to bring about crystallization of bicalutamide is about 25° C.

Preferably, in this embodiment, first solvent: second solvent system combinations include DMF:water and ethyl acetate:hexane.

In another embodiment, the present invention provides a process for the purification and isolation of bicalutamide by solution crystallization, comprising the steps of:
(i) combining crude bicalutamide and a first solvent, wherein the first solvent is an anti-solvent;
(ii) adding a second solvent to the crude bicalutamide-first solvent mixture;
(iii) crystallizing the bicalutamide from the solvents; and
(iv) collecting the crystals of bicalutamide.

Preferably, in this embodiment, the crude bicalutamide is adedd to the first solvent, or anti-solvent, and the resulting bicalutamide suspension is heated to about the boiling point of the first solvent. Preferably, in this embodiment, the addition of the second solvent, or anti-solvent, takes place under reflux conditions, with the second solvent being added in an amount sufficient to dissolve the bicalutamide.

Preferably the crystallizing step comprises cooling the bicalutamide solution to a temperature sufficient to bring about crystallization of bicalutamide. Most preferably the temperature sufficient to bring about crystallization of bicalutamide is about 25° C.

Preferably, in this embodiment, the first solvent, or anti-solvent is selected from the group consisting of toluene, ether, chloroform, water, methanol and ethanol.

Preferably, in this embodiment, the second solvent is selected from the group consisting of acetonitrile, acetone, THF, DMF and isobutyl methyl ketone.

According to another object, the present invention provides a process for the purification and isolation of bicalutamide by solution crystallization, comprising the steps of:
(i) combining bicalutamide and a first solvent;
(ii) adding a second solvent to the bicalutamide-first solvent mixture;
(iii) crystallizing the bicalutamide from the solvents with or without seeding; and
(iv) collecting the crystals of bicalutamide.

According to another object, the present invention provides a process for the purification and isolation of bicalutamide by solution crystallization, wherein the solvents utilized have low toxic potential.

The present invention also provides rac-bicalutamide and its intermediates prepared and isolated by the processes described above.

DETAILED DESCRIPTION OF THE INVENTION

Definitions:

As used herein, rac-bicalutamide refers to both the R-(−) enantiomer and S-(+) enantiomer of bicalutamide. Rac-bicalutamide is the racemic and optically pure R-(−) and S-(+) isomers of N-[4-cyano-3-trifluoromethyl-phenyl]-3-[4-fluorophenyl-sulfonyl]-2-hydroxy-2-methyl-propionamide. It is to be understood that this invention encompasses the racemic form of bicalutamide and any optically-active form which possesses anti-androgenic activity. It is a matter of common general knowledge how a racemic compound may be resolved into its optically-active forms and how any anti-androgenic activity present in any of these forms may be determined. One skilled in the art will appreciate that the separation of optical isomers can be achieved by conventional resolution; such as fractional crystallization or flash-chromatography.

As used herein, the term "micronized" refers to particles having a mean particle diameter of less than about 200 μm.

As used herein, the term "μm" refers to "micrometer" which is $1 \times 10^{-6}$ meter.

As used herein, the term "anti-solvent" refers to a solvent in which bicalutamide has limited or no solubility.

As used herein, the term "crude bicalutamide" refers to the product prepared by a process to prepare bicalutamide.

The following abbreviations are used herein: DCM is dichloromethane. THF is tetrahydrofuran. DABCO is 1,4 dizazbicyl [2.2.2] octane. ACB is 5-amino-2-cyano-benzotrifluoride. BCL is rac-bicalutamide. 4-FPMS is 4-fluorophenyl methyl sulfone. DMF is N,N dimethyl formamide. DMSO is dimethyl sulfoxide.

The present invention provides a novel process for preparing rac-bicalutamide from ethyl pyruvate and 4-fluorophenyl methyl sulfone via the formation of an intermediate with chemical formula of [X].

The present invention further provides a novel process for preparing preparing rac-bicalutamide from 4-fluorophenyl methyl sulfone. Butyl lithium reacts with 4-fluorophenyl methyl sulfone with a base to form an organo lithium intermediate (i.e., with chemical formula of [X]), optionally in the presence of anion stabilizer such as DABCO. The base refers to strong bases such as lithium diisopropyl amid (LDA) or its derivatives. This reaction is preferably carried out in an inert solvent, for example tetrahydrofuran or diethyl ether. A most preferable solvent is tetrahydrofuran. The reaction is preferably carried out at a low temperature, for example −40° C. to 10° C. Most preferable temperature is between −2° C. and 2° C.

Figure 1:
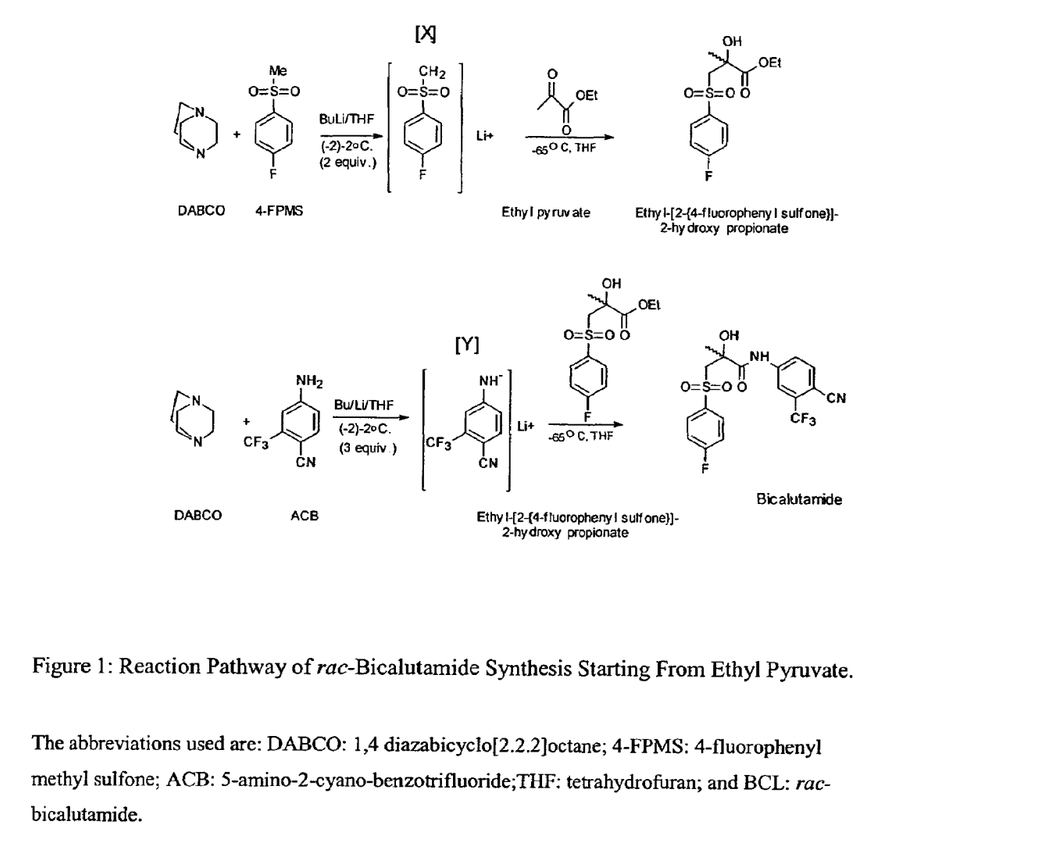
FIG. 1 depicts the reaction pathway of rac-bicalutamide synthesis starting from ethyl pyruvate.

FIG. 1 illustrates the schematic process for preparing rac-bicalutamide from ethyl pyruvate and 4-fluorophenyl methyl sulfone. The intermediate with general chemical formula of [X] reacts with ethyl pyruvate to form ethyl-[2-4-{4-fluorophenyl sulfone}]-2-hydroxy propionate. This reaction is preferably carried out in an inert organic solvent, for example tetrahydrofuran or diethyl ether. Most preferable solvent is tetrahydrofuran. The reaction is preferably carried out at a low temperature, for example −60° C. to −100° C. Most preferable temperature is −60° C.

The present invention provides a process of preparing rac-bicalutamide from 5-amino-2-cyano-benzotrifluoride. Butyl lithium reacts with 5-amino-2-cyano-benzotrifluoride with a base to form an organo lithium intermediate (i.e., with chemical formula of [Y]), optionally in the presence of an anion stabilzer such as DABCO. The base refers to strong bases such as LDA or its derivatives. This reaction is preferably carried out in an inert organic solvent, for example tetrahydrofuran or diethyl ether. A most preferable solvent is tetrahydrofuran. The reaction is preferably carried out at a low temperature, for example −40° C. to 10° C. Most preferable temperature is between −2° C. and 2° C.

The present invention provides a process of preparing rac-bicalutamide from 5-amino-2-cyano-benzotrifluoride via intermediate with chemical formula of [Y]. Intermediate with chemcial formula [Y] thus formed reacts with rac-ethyl-[2-{4-fluorophenyl sulfone}]-2-hydroxy propionate to form rac-bicalutamide. This reaction is preferably carried out in an inert organic solvent, for example tetrahydrofuran or diethyl ether. Most preferable solvent is tetrahydrofuran. The reaction is preferably carried out at a low temperature, for example −60° C. to −100° C. Most preferable temperature is −60° C.

The detailed procedures of preparing rac-ethyl-[2-{4-fluorophenyl sulfone}]-2-hydroxy propionic acid from ethyl pyruvate and 4-fluorophenyl methyl sulfone as well as rac-bicalutamide from rac-ethyl-[2-{4-fluorophenyl sulfone}]-2-hydroxy propionic acid and 5-amino-2-cyano-benzotrifluoride are illustrated in FIG. 1.

Crystallization of Crude Bicalutamide

The present invention provides a process for the purification and isolation of bicalutamide. The process of the invention comprises the steps of:
(i) combining crude bicalutamide and a solvent;
(ii) crystallizing the bicalutamide from the solvent with or without seeding; and
(iii) collecting the crystals of bicalutamide.

The crude bicalutamide may or may not be substantially soluble in the solvent. Preferably the crude bicalutamide is soluble in the solvent. Preferably the crude bicalutamide is dissolved in the solvent and the resulting bicalutamide solution or suspension is crystallized by applying agitation for a time sufficient to bring about crystallization of the bicalutamide. The duration of the agitation may be from about 1 hour to about 48 hours. Preferably the duration of the agitation is from about 8 hours to about 15 hours. The agitation may be brought about by any means known to the skilled artisan. The agitation may be accompanied by heating of the reaction mixture. Preferably, the agitation is carried out at room temperature.

Preferably the solvent is selected from the group consisting of water, methanol, ethanol, DCM, toluene, PE, chloroform, hexane, 1,2-dichloroethane, diethyl ether, propanol and isopropanol.

According to another embodiment of the invention, the novel process for the purification and isolation of bicalutamide by solution crystallization, comprises the steps of:
(i) combining crude bicalutamide and a first solvent;
(ii) adding a second solvent to the crude bicalutamide-first solvent mixture;
(iii) crystallizing the bicalutamide from the solvents with or without seeding; and
(iv) collecting the crystals of bicalutamide.

The first solvent and the second solvents may be the same or different. In one embodiment of the invention, the first and second solvents are the same. Preferably the crude bicalutamide is dissolved in an amount of first solvent sufficient to dissolve the bicalutamide. Preferably the resulting bicalutamide solution is heated to about the boiling point of the first solvent.

Preferably, the amount of second solvent added to the bicalutamide solution is equal to that of the first volume. The second solvent is preferably added under reflux conditions.

Preferably the crystallizing step comprises cooling the bicalutamide solution to a temperature sufficient to bring about crystallization of bicalutamide with or without seeding. Most preferably the temperature sufficient to bring about crystallization of bicalutamide is about 25° C.

The term "seeding" refer to the addition of a crystal of the product to the product solution in order to bring about crystallization, or scratching the inner surface of the crystallization vessel with a glass rod. The present invention covers embodiments where crystallization or precipitation occurs spontaneously, or is induced/accelerated Preferably the first and second solvents are selected from the group consisting of water, methanol, ethanol, ethyl acetate, acetonitrile, acetone, THF, propanol, DMF, DMSO and isobutyl methyl ketone.

In another embodiment, the present invention provides a novel process for the purification and isolation of bicalutamide by solution crystallization, comprising the steps of:
(i) combining crude bicalutamide and a first solvent;
(ii) adding a second solvent to the crude bicalutamide-first solvent mixture, wherein the second solvent is an anti-solvent;
(iii) crystallizing the bicalutamide from the solvents; and
(iv) collecting the crystals of bicalutamide.

Preferably the crude bicalutamide is dissolved in an amount of first solvent sufficient to dissolve the bicalutamide. The the resulting bicalutamide solution is heated to about the boiling point of the first solvent. Preferably the addition of the second solvent, or anti-solvent, takes place under reflux conditions, with the second solvent being added in an amount sufficient to bring about an at least partially desolubilized bicalutamide. The partial desolubilization is accompanied by the formation of a clouody appearance in the clear solution.

Following addition of the second solvent, a small volume of first solvent, sufficient to dissolve the at least partially desolubilized bicalutamide is added to the mixture. Sufficient volume of the first solvent is added when the cloudy solution becomes clear.

Preferably the crystallizing step comprises cooling the bicalutamide solution to a temperature sufficient to bring about crystallization of bicalutamide. Most preferably the temperature sufficient to bring about crystallization of bicalutamide is about 25° C.

Preferably the first solvent: second solvent systems are selected from the group consisting of DMF: water and ethyl acetate: hexane.

In another embodiment, the present invention provides a novel process for the purification and isolation of bicalutamide by solution crystallization, comprising the steps of:
(i) combining crude bicalutamide and a first solvent, wherein the first solvent is an anti-solvent;
(ii) adding a second solvent to the crude bicalutamide-first solvent mixture;
(iii) crystallizing the bicalutamide from the solvents with or without seeding; and
(iv) collecting the crystals of bicalutamide.

Preferably the crude bicalutamide is adedd to the first solvent, or anti-solvent, and the resulting bicalutamide suspension is heated to about the boiling point of the first solvent. The addition of the second solvent, or anti-solvent, takes place under reflux conditions, with the second solvent being added in an amount sufficient to dissolve the bicalutamide.

Preferably the crystallizing step comprises cooling the bicalutamide solution to a temperature sufficient to bring about crystallization of bicalutamide. Most preferably the temperature sufficient to bring about crystallization of bicalutamide is about 25° C.

Preferably the first solvent, or anti-solvent is selected from the group consisting of toluene, ether, chloroform, water, methanol and ethanol.

Preferably the second solvent is selected from the group consisting of acetonitrile, acetone, THF, DMF and isobutyl methyl ketone.

In another embodiment, the novel processes for the purification and isolation of bicalutamide by solution crystallization of the present invention are carried out using solvents having low toxic potential. Suitable solvents are described as Class III solvents in the ICH Harmonized Tripartite Guideline, Impurities: Guideline for Residual Solvents. Class III solvents are described as being regarded as less toxic and of lower risk to human health, and include no solvent known as a human health hazard at levels normally accepted in pharmaceuticals. Class III solvents acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate and tetrahydro furan.

The process according to our invention is described in detail by the following, but not limiting, examples.

EXAMPLE 1

Preparation of rac-ethyl-[2-{4-fluorophenyl sulfone}]-2-hydroxy Propionic Acid 4-fluorophenyl methyl sulfone (4-FPMS) (5 g, 27.8 mmol) and 1,4 diazabicyclo[2.2.2]octane (DABCO) (3.2 g, 28.5 mmol) were dissolved in tetrahydrofuran (THF) and cooled in a dry-ice acetone bath to about −2° C.

A 2.5 M solution of butyl lithium in hexanes (14.5 mL, 36.2 mmol) was added to the cold THF solution dropwise via a syringe keeping the temperature between about −2° C. to about 2° C. After addition was completed the stirring was continued for about 1 hour while maintaining the temperature at about −2° C. Then, the temperature was lowered to about −65° C. and a solution of ethyl pyruvate (3.67 g, 31.6 mmol) in THF (30 mL) was added dropwise.

After addition was completed, the stirring was continued for an hour at temperatures between about −65° C. and about −30° C. and then followed by an addition of 2N HCl (30 mL) dropwise to the reaction mixture at about −30° C. The reaction was allowed to warm-up to room temperature and the mixture was evaporated in vacuo on a rotary evaporator to remove THF and ethanol.

The residual solution was extracted with diethyl ether (3×100 mL). The combined ether extracts were dried over $Na_2SO_4$, filtered and the filtrate was completely evaporated to give a crude oil.

The product was purified by column chromatography on silica gel via eluting with dichloromethane (DCM) to give rac-ethyl-[2-{4-fluorophenyl sulfone}]-2-hydroxy propionic acid as a colorless oil.

The purified product was characterized by a $^1H$ NMR (500 MHz, $CDCl_3$): 7.92 (m, 2H), 7.22 (m, 2H), 4.29 (m, 2H, $OCH_2$), 3.77 (d, J=15 Hz, 1H, $CH_{2\alpha}$), 3.68 (bs, 1H, OH), 3.55 (d, J=15 Hz, 1H, $CH_{2\beta}$), 1.45 (s, 3H, Me), 1.35 (t, J=7 Hz, 3H, $OCH_2CH_3$).

The purified product was further characterized by a $^{13}C$ NMR (125.7 MHz, $CDCl_3$): 174.7 ($CO_{ester}$), 166.4 (C-4', $J_{C-F}$=258 Hz), 137.5 ((c-1'), 131.7 (C-2',6', $J_{C-F}$=9 Hz), 117.0 (C-3',5', $J_{C-F}$=21.6 Hz), 72.9 ($C_{quat}$), 64.6 ($CH_2$), 63.6 ($OCH_2$), 27.9 ($CH_3$), 14.7 ($OCH_2CH_3$).

The purified product was further characterized by HPLC (acetonitrile:water 1:1 with 0.01% TFA): 5.4 mins.

EXAMPLE 2

Preparation of rac-N-[4-cyano-3-trifluoromethyl-phenyl]-3-[4-fluorophenyl sulfonyl]-2-hydroxy-2-methyl-propionamide 5-amino-2-cyano-benzotrifluoride (ACB) (0.27 g, 1.45 mmol) and 1,4 diazabicyclo[2.2.2]octane (DABCO) (0.32 g, 2.85 mmol) were dissolved in tetrahydrofuran (THF) (30 mL) and cooled in dry-ice acetone bath to about −2° C.

A 2.5M solution of butyl lithium in hexanes (2 mL, 5 mmol) was added to the cold THF solution dropwise via a syringe keeping the temperature between about −2° C. to about 2° C. After addition was completed, the stirring was continued for 1 hour while maintaining the temperature at about −2° C. The temperature was then lowered to about −65° C. and a solution of rac-Ethyl-[2-{4-fluorophenyl sulfone}]-2-hydroxy propionate (0.34 g, 1.17 mmol) in THF (20 mL) was added dropwise.

After addition was completed, the stirring was continued for an hour at temperatures between about −65° C. and about −30° C. after which 2N HCl (30 mL) was added dropwise to the reaction mixture at about −30° C. The reaction was allowed to warm-up to room temperature and the mixture was evaporated in vacuo on a rotary evaporator to remove THF and ethanol.

The residual material was extracted with diethyl ether (3×100 mL). The combined ether extracts were dried over $Na_2SO_4$, filtered and the filtrate was completely evaporated to give a crude oil.

The product was purified by column chromatography on silica gel eluting with ethyl acetate-petroleum ether to give rac-N-[4-cyano-3-trifluoromethyl-phenyl]-3-[4-fluorophenyl sulfonyl]-2-hydroxy-2-methyl-propionamide in about 40% yield, as a pale yellow solid.

Figure 2:
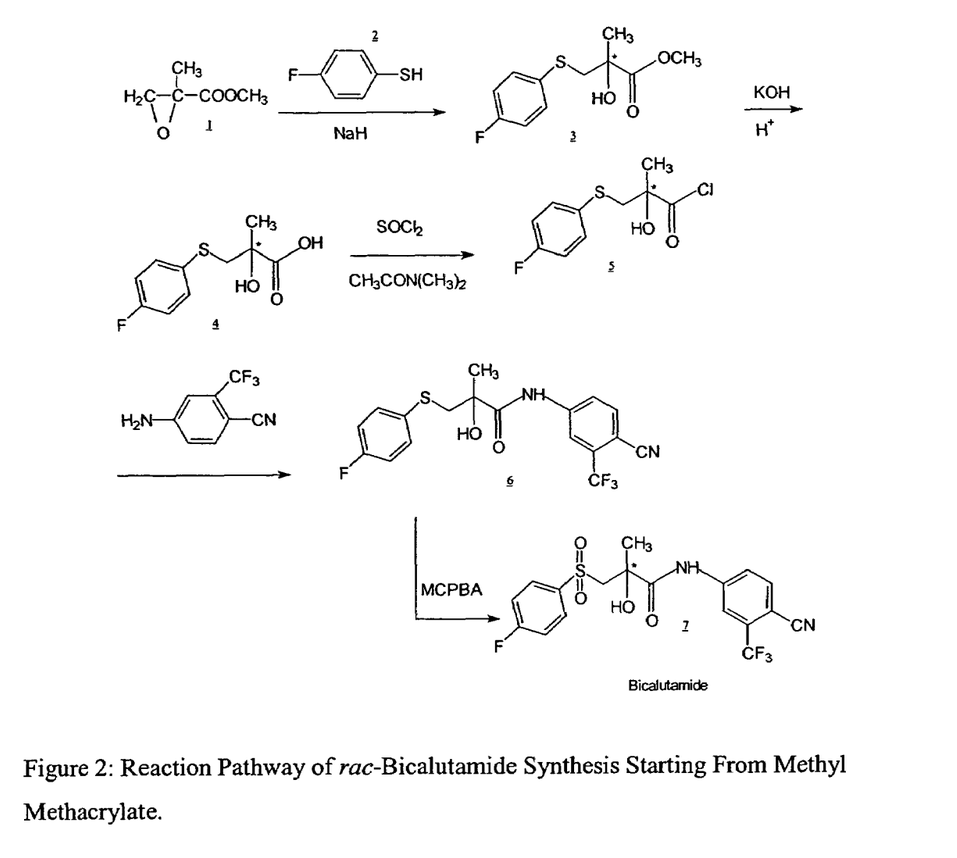
FIG. 2 depicts the reaction pathway of rac-bicalutamide synthesis starting from methyl methacrylate.

The present invention further provides a novel process for preparing rac-bicalutamide from methyl methacrylate. FIG. 2 illustrates the schematic process for preparing rac-bicalutamide from methyl methacrylate.

According to FIG. 2, the starting material was methyl methacrylate, which can usually be converted into the epoxide only under harsh conditions (i.e. with peracetic acid in ethyl acetate at 75° C. [J. A. Chem., 81, 680 (1959)], or with 90% hydrogen peroxide-trifluoroacetic anhydride at 40° C. [J. Am. Chem., 77, 89 (1955)], or with MCPBA in dichloromethane at 0° C. in low yield [J. Med. Chem., 29, 2184 (1986)]. The epoxidation under these conditions can be explosive. The present invention describes this oxidation using Oxone®.

The methyl 2-methyl-oxirane-carboxylate of formula (1), which was obtained by epoxidation, was reacted with 4-fluorothiophenol [formula (2)] in the presence of sodium hydride under the conditions listed in Scheme-2. The obtained methyl 2-hydroxy-2-methyl-3-(4-fluorophenylthio)-propionate of formula (3) was hydrolyzed with potassium hydroxide in aqueous ethanol over a period of 22 hours to yield the 2-hydroxy-2-methyl-3-(4-fluorophenylthio)-propionic acid of formula (4), which was converted into acid chloride of formula (5) with thionyl chloride in dimethyl acetamide at −15° C.

The obtained acid chloride was reacted with 4-amino-2-trifluoromethyl-benzonitrile in dimethylacetamide at −15° C. to yield the thioether derivative of formula (6). The oxidation of the thioether derivative was carried out by known method with m-chloroperbenzoic acid in dichloromethane to yield the final product, bicalutamide, of formula (7).

The process according to our invention is illustrated in detail by the following, but not limiting, examples.

EXAMPLE 3

Preparation of Methyl 1,2-epoxy-2-methyl-propionate

In a 3L four-neck round bottom flask, Oxone® (50% $KHSO_5$, 227 grams, 0.75 mol) was dissolved in water (1L) and 10 M KOH was added to adjust the pH to ~6 (~53 mL). Then, methyl methacrylate (13 mL, 0.122 mol) in methanol was added (50 mL) followed by 360 mL of water.

The solution was stirred at room temperature and pH was continuously adjusted to pH=6 with 1M KOH (~270 mL). After 6 hr the reaction was stirred over night. Then, 2N HCl was added (100 mL, pH=3) and the entire aqueous solution was extraced with DCM (dichloromethane) (3×150 mL) for each 400 mL reaction solution. The combined DCM extracts were washed with saturated sodium sulfite solution followed by saturated sodium bicarbonate solution.

After drying and filtartion, DCM was removed under distillation and the unreacted methyl methacrylate was distilled out. The residue contained the product as an oily material.

GC: (>97%, 1.45 min); yield: 66%; $^1H$ NMR (500 MHz, $CDCL_3$; □ ppm 3.72 (s,3H, Me), 3.07 (dd, J=6 Hz,, J=16 Hz, 1H, $H_□$), 2.73 (d, J=6 Hz, 1H, $H_□$), 1.55 (s, Me); $^{13}C$-NMR (125.7 MHz, $CDCL_3$; □ ppm): 172 ($CO_{ester}$), 54.3 ($CH_2$), 53.6 ($C_{quat}$), 53.2 ($Me_{ester}$), 18 (Me).

EXAMPLE 4

Preparation of 2-hydroxy-2-methyl-3-(4-fluorophenylthio) Propionic Acid

To a solution of 4-fluorothiophenol (1 mL) in MeOH (32 mL) was added dropwise 2N NaOH$_{aq.}$ (16 mL) under N$_2$, while the temperature was kept at 25° C. during the addition period. When addition was completed, the reaction mixture was stirred at room temperature for further 90 min.

A solution of methyl-1,2-epoxy-2-methyl propionate (1.2 gram) in MeOH (20 mL) was then added dropwise at room temperature. When addition was completed, the reaction mixture was stirred over night at ambient temperature. To the reaction mixture 2N HCl (20 mL) was added followed by ethyl acetate (60 mL). The organic phase was separated. The aqueous phase (pH~2) was washed with 60 mL of chloroform and then discarded. The ethyl acetate and chloroform extracts were combined.

After drying (MgSO$_4$) and filtration, the two organic solvents were evaporated to leave an oily product which solidified upon standing at room temperature.
Purity: 75% (according to GC); Yield: 66%. GCMS: 230 m/z (13%); M.p.: 69.1–72.7° C.; $^1$H NMR (500 MHz, CDCL$_3$; □ ppm 7.43 (m, 2H, H-2',6'), 6.96 (m, 2H, H-3',5'), 3.39 (d, J=14 Hz, 1H, H$_□$), 3.17 (d, J=14 Hz, 1H, H$_□$), 1.53 (s, Me); $^{13}$C-NMR (125.7 MHz, CDCL$_3$; □ ppm): 180.4 (CO$_{acid}$), 162.6 (d, J$_{C-F}$=248 Hz, C-4'), 134.3 (d, J$_{C-F}$=7.5 Hz, C-2',6'), 130.8 (d, J$_{C-F}$=3.2 Hz, C-1'), 116.5 (d, J$_{C-F}$=21.6 Hz, C-3',5'), 75.2 (C$_{quat}$), 53.3 (Me$_{ester}$), 46.4 (CH$_2$), 26.0 (Me).

EXAMPLE 5

Crystallization Methods for Preparation of Purified Bicalutamide

Example 5A

Crude bicalutamide (260 g) was dissolved in ethanol (5 L) at reflux temperature, and water (7.5 L) was added gradually over a period of 1.5–2 hours to precipitate the product. The slurry was cooled to 0–5° C. and stirred for 2 hours. The precipitate was collected, washed with water (625 mL), and dried at 60° C. in a vacuum oven to yield the crystalline bicalutamide (252.5 6 g, 94% for two steps).
Purity: 99.94%
Assay: 99.4%
Water: 0.11%
Ethanol: 142 ppm

Example 5B

A sample of rac-bicalutamide (1.5 g, 3.45 mmol) was dissolved in a minimum volume of a solvent and then boiled. Under reflux conditions, an additional volume of the same solvent was added until the solution was clear and no precipitate was observed. Following the addition of solvent, the solution was cooled to room temperature and left to stand over-night.

The crystals were filtered off and dried in an oven at 70° C. under vacuum.

Solvent systems:
1. Ethyl acetate (20 mL)
2. Acetonitrile (5 mL)
3. Acetone (7.2 mL)
4. THF (7.2 mL)
5. n-Propanol (27 mL)
6. DMF (2.2 mL)
7. DMSO (2.2 mL)
8. Isobutyl methyl ketone (2.2 mL)

Example 5C

Bicalutamide was dissolved in a suitable solvent in which it is readily soluble (minimum volume under reflux) and then an anti-solvent was added until a cloudy solution was formed. A few drops of the solvent were then added to clear the solution again and the solution was cooled to room temperature and left to stand overnight.

The crystals were filtered off and dried in an oven at 70° C. under vacuum.

Solvent systems:
1. DMF (12 mL): water (18 mL)
2. Ethyl acetate (33 mL): hexane (6 mL)

Example 5D

A suspension of bicalutamide in an anti-solvent was prepared (fixed volume under reflux) and then a highly solublizing solvent was added until a clear solution was formed and all the precipitate disappeared. The solution was then cooled to room temperature and left to stand overnight.

The crystals were filtered off and dried in an oven at 70° C. under vacuum.

Solvent Systems:
1. Toluene (50 mL): acetonitrile (4 mL)
2. Ether (50 mL): acetonitrile (36 mL)
3. Chloroform (50 mL): acetonitrile (13 mL)
4. Water (10 mL): acetonitrile (14 mL)
5. Water (10 mL): acetone (26 mL)
6. Water (10 mL): THF (36 mL)
7. Methanol (10 mL): acetonitrile (5 mL)
8. Methanol (10 mL): acetone (4 mL)
9. Methanol (10 mL): THF (4 mL)
10. Methanol (10 mL): DMF (12.4 mL)
11. Ethanol (10 mL): THF (6.4 mL)
12. Ethanol (10 mL): DMF (12.4 mL)
13. Ethanol (10 mL): Isobutyl methyl ketone (12.4 mL)

Example 5E

Trituration Procedure

A sample of rac-bicalutamide (~1 g, 2.3 mmol) was suspended in a fixed volume (30 mL) of a solvent and stirred vigorously at room temperature overnight.

The crystals were filtered off and dried in an oven at 70° C. under vacuum.

Solvent Systems:
1. Water (30 mL)
2. Methanol (30 mL)
3. Ethanol (30 mL)
4. DCM (30 mL)
5. Toluene (30 mL)
6. Petroleum ether (30 mL)
7. Chloroform (30 mL)
8. n-Hexane (30 mL)
9. 1,2-Dichloroethane (30 mL)

10. Diethyl ether (30 mL)
11. n-Propanol (30 mL)
12. Iso-propanol (30 mL)

Micronized rac-bicalutamide

The Particle Size Distribution (PSD) of rac-bicalutamide may be used to determine the available surface area for the drug dissolution. Often, it is observed that the available surface area for drug dissolution correlates to both (a) the rate of dissolution and solubility where a great surface area enhances the solubility of a drug; and (b) enhances the rate of dissolution of a drug. The rate of dissolution of a drug effects the drug's bioavailability. Thus, the PSD of rac-bicalutamide, and in particular, the meagrn particle diameter, are important parameters to characterize and predict the bioavailibility of rac-bicalutamide.

The present invention provides rac-bicalutamide formulations containing rac-bicalutamide having relative small particles and corresponding relatively large surface area.

The present invention provides rac-bicalutamide formulations containing rac-bicalutamide having a mean particle diameter of less than 200 µm, preferably the mean particle diameter is less than 100 µm, more preferably the mean particle diameter is less than 20 µm, and most preferably the mean particle size is about 10 µm.

The present invention provides rac-bicalutamide having a mean particle diameter of between about 200 µm and about 10 µm. In one embodiment of the invention, rac-bicalutamide has a mean diameter of about 4.2 µm, more preferably a mean diameter of 4.0 µm.

The present invention also provides process for preparing micronized rac-bicalutamide. By the methods of the present invention, rac-bicalutamide, which is prepared by methods known in the art, is separated by sieves to produce rac-bicalutamide wherein 50% has a mean particle diameter of below about 250 µm and about 80% has a mean particle diameter of below about 500 µm. The sieved rac-bicalutamide is then micronized by methods known in the art, e.g., in a micronizer, to yield rac-bicalutamide wherein 100% of rac-bicalutamide has a mean particle size of less than about 45 µm, preferably 99% of the rac-bicalutamide has a mean particle size of less than about 45 µm, more preferably, 93% of the rac-bicalutamide has a mean particle size of less than about 7.5 µm, more preferably the rac-bicalutamide isolated has a mean particle diameter of less than about 10 µm.

Micronized particles of rac-bicalutamide can be obtained by the use of conventional micronizing techniques after sieving to provide rac-bicalutamide wherein about 50% has a particle size of less than about 250 µm and about 80% has a particle size of less than 500 µm. By the methods of the present invention, the rac-bicalutamide where about 50% has a particle size less than 500 µm and about 80% has a particle size below about 500 µm, is micronized to the desired particle size range by methods known in the art, for example, using a ball mill, ultrasonic means, fluid energy attrition mills, or using a jet mill, or other suitable means as disclosed in *Pharmaceutical Dosage Forms*: Tablets, Vol. 2, 2$^{nd}$ Ed., Lieberman et al. Ed., Marcel Dekker, Inc. New York (1990) p. 107–200, the content of which is incorporated by reference herein.

The present invention provides micronized rac-bicalutamide as pharmaceutical compositions that are particularly useful for its anti-androgen activity. Such compositions comprise micronized rac-bicalutamide with pharmaceutically acceptable carriers and/or excipients known to one of skilled in the art.

Preferably, these compositions are prepared as medicaments to be administered orally or intravenously. Suitable forms for oral administration niclude tablets, compressed or coated pills, dragees, sachets, hard or gelatin capsules, sub-lingual tablets, syrups and suspensions. While one of ordinary skill in the art will understand that dosages will vary according to the indication, age and severity of the disease of the patent etc., generally micronized rac-bicalutamide of the present invention will be administered at a daily dosage of about 2 mg to about 200 mg per day, and preferably about 5 mg to about 100 mg per day.

What is claimed is:

1. A process for the purification and isolation of bicalutamide, comprising the steps of:
   (i) combining crude bicalutamide and a solvent selected from the group consisting of water, methanol, ethanol, propanol, and isopropanol;
   (ii) crystallizing the bicalutamide from the solvent; and
   (iii) collecting the crystals of bicalutamide.

2. The process of claim 1, wherein the the crystallizing step (ii) comprises seeding the bicalutamide suspension.

3. The process of claim 1, further comprising heating the resulting bicalutamide solution to about the boiling point of the solvent.

4. The process of claim 1, wherein the solvent is selected from the group consisting of ethanol, propanol and isopropanol.

5. A process for the purification and isolation of bicalutamide, comprising the steps of:
   (i) combining crude bicalutamide and a first solvent;
   (ii) adding a second solvent to the crude bicalutamide-first solvent mixture;
   (iii) crystallizing the bicalutamide from the solvents; and
   (iv) collecting the crystals of bicalutamide, wherein the first solvent and second solvent are different, the second solvent is an anti-solvent selected from the group consisting of water, methanol, ethanol and propanol, and the first solvent is selected from the group consisting of acetonitrile, acetone, tetrahydrofuran, dimethylformamide, dimethyl sulfoxide and isobutyl methyl ketone.

6. The process of claim 5, further comprising heating the bicalutamide solution of step (i) to about the boiling point of the first solvent.

7. The process of claim 6, wherein the addition of the second solvent takes place under reflux conditions.

8. The process of claim 5, wherein the crystallizing step comprises cooling the bicalutamide solution to a temperature sufficient to bring about crystallization of bicalutamide.

9. The process of claim 8, wherein the the crystallizing step comprises seeding the bicalutamide suspension.

10. The process of claim 8, wherein the temperature sufficient to bring about crystallization of bicalutamide is about 25° C.

11. The process of claim 8, wherein the second solvent is selected from the group consisting of water, methanol and ethanol.

12. The process of claim 5, wherein the second solvent is selected from the group consisting of ethanol and propanol.

13. The process of claim 11, wherein the amount of the first solvent is sufficient to dissolve the crude bicalutamide.

14. The process of claim 11, wherein the first solvent is dimethylformamide and the second solvent is water.

15. The process of claim 11, wherein the amount of the second solvent is added in an amount sufficient to bring about an at least partially desolubilized bicalutamide.

16. The process of claim 15, further comprising, following addition of the second solvent, adding a volume of the first solvent sufficient to dissolve the at least partially desolubilized bicalutamide.

17. A process for the purification and isolation of bicalutamide, comprising the steps of:
(i) combining crude bicalutamide and a first solvent;
(ii) adding a second solvent to the crude bicalutamide-first solvent mixture;
(iii) crystallizing the bicalutamide from the solvents; and
(iv) collecting the crystals of bicalutamide, wherein the first solvent is ethanol and the second solvent is water.

18. The process of claim 17, wherein the temperature sufficient to bring about crystallization of bicalutamide is about 25° C.

19. A process for the purification and isolation of bicalutamide, comprising the steps of:
(i) combining crude bicalutamide and a first solvent; wherein the first solvent is an anti-solvent selected from the group consisting of water, methanol and ethanol;
(ii) adding a second solvent to the crude bicalutamide-first solvent mixture, wherein the second solvent is selected from the group consisting of acetonitrile, acetone, tetrahydrofuran, dimethylformamide and isobutyl methyl ketone;
(iii) crystallizing the bicalutamide from the solvents; and
(iv) collecting the crystals of bicalutamide.

20. The process of claim 19, wherein the first solvent is water, and the second solvent is selected from the group consisting of acetone and tetrahydrofuran.

21. The process of claim 19, wherein the first solvent is methanol, and the second solvent is selected from the group consisting of acetone, tetrahydrofuran and dimethylformamide.

22. The process of claim 19, wherein the first solvent is ethanol, and the second solvent is selected from the group consisting of tetrahydrofuran, dimethylformamide and isobutyl methyl ketone.

23. The process of claim 19, wherein the second solvent is added in an amount sufficient to dissolve the bicalutamide.

24. The process of claim 19, further comprising heating the bicalutamide solution formed in step (i) to about the boiling point of the first solvent.

25. The process of claim 24, wherein the addition of the second solvent takes place under reflux conditions.

26. The process of claim 19, wherein the crystallizing step comprises cooling the bicalutamide solution to a temperature sufficient to bring about crystallization of bicalutamide.

27. The process of claim 26, wherein the the crystallizing step comprises seeding the bicalutamide solution.

28. The process of claim 27, wherein the temperature sufficient to bring about crystallization of bicalutamide is about 25° C.

29. A method of preparing rac-bicalutamide, comprising the steps of:
(i) preparing a mixture of 5-amino-2-cyano-benzotrifluoride and butyl lithium in an organic solvent;
(ii) adding ethyl-[2-{4-fluorophenyl sulfone}]-2-hydroxy propionic acid to the mixture; and
(iii) isolating rac-bicalutamide by use of a process for purifying and isolating bicalutamide comprising the steps of:
(a) combining crude bicalutamide and a solvent;
(b) crystallizing the bicalutamide from the solvent; and
(c) collecting the crystals of bicalutamide.

30. A method of preparing rac-bicalutamide, comprising the steps of:
(i) preparing a mixture of 5-amino-2-cyano-benzotrifluoride and butyl lithium in an organic solvent;
(ii) adding ethyl-[2-{4-fluorophenyl sulfone}]-2-hydroxy propionic acid to the mixture; and
(iii) isolating rac-bicalutamide by use of a process for purifying and isolating bicalutamide comprising the steps of:
(a) combining crude bicalutamide and a first solvent;
(b) adding a second solvent to the crude bicalutamide-first solvent mixture;
(c) crystallizing the bicalutamide from the solvents; and
(d) collecting the crystals of bicalutamide.

31. A method of preparing rac-bicalutamide, comprising the steps of:
(i) preparing a mixture of 5-amino-2-cyano-benzotrifluoride and butyl lithium in an organic solvent;
(ii) adding ethyl-[2-{4-fluorophenyl sulfone}]-2-hydroxy propionic acid to the mixture; and
(iii) isolating rac-bicalutamide by use of a process for purifying and isolating bicalutamide comprising the steps of:
(a) combining crude bicalutamide and a first solvent; wherein the first solvent is an anti-solvent;
(b) adding a second solvent to the crude bicalutamide-first solvent mixture;
(c) crystallizing the bicalutamide from the solvents; and
(d) collecting the crystals of bicalutamide.

32. The process of claim 19, wherein the second solvent is acetonitrile.

* * * * *

UNITED STATES PATENT AND TRADEMARK OFFICE
CERTIFICATE OF CORRECTION

| | |
|---|---|
| PATENT NO. | : 7,102,026 B2 |
| APPLICATION NO. | : 10/606403 |
| DATED | : September 5, 2006 |
| INVENTOR(S) | : Ben-Zion Dolitzky et al. |

It is certified that error appears in the above-identified patent and that said Letters Patent is hereby corrected as shown below:

Column 1,
Line 8, change "continuation-in-part of patent" to --continuation-in-part application of patent--
Lines 60-62, change "N-[4-cyano-3-trifluoromethylphenyl]-3-[4-fluorophenyl-sulfonyl]-2-hydroxy-2-methyl-proprionamide" to --N-[4-cyano-3-trifluoromethyl-phenyl]-3-[4-fluorophenyl-sulfonyl]-2-hydroxy-2-methyl-proprionamide--.

Column 2,
Line 4, change "environmental" to --environmentally--;
Line 37, change "a precess for preparing" to --a process for preparing--;
Line 56, change "stablizied" to --stabilized--;
Line 62, change "benzotrifloride" to --benzotrifluoride--.

Column 5,
Line 64, change "preparing preparing" to --preparing--.

Column 7,
Line 31, change "refer" to --refers--;
Line 53, change "The the" to --The--;
Line 59, change "clouody" to --cloudy--.

Column 8,
Line 44, change "Class III solvents acetic acid" to --Class III solvents include acetic acid--.

Column 10,
Line 58, change "filtartion" to --filtration--.

Column 11,
Line 61, change "over-night" to --overnight--.

Column 13,
Line 14, change "meagrn" to --mean--;
Line 29, change "mean diameter" to --mean particle diameter--;
Line 30, change "mean diameter" to --mean particle diameter--.

UNITED STATES PATENT AND TRADEMARK OFFICE
CERTIFICATE OF CORRECTION

PATENT NO.         : 7,102,026 B2
APPLICATION NO. : 10/606403
DATED              : September 5, 2006
INVENTOR(S)        : Ben-Zion Dolitzky et al.

It is certified that error appears in the above-identified patent and that said Letters Patent is hereby corrected as shown below:

Column 14,
Line 3, change "niclude" to --include--;
Line 8, change "patent" to --patient--.

In Claim 2,
Line 1, change "the the" to --the--.

Signed and Sealed this

Eleventh Day of March, 2008

JON W. DUDAS
*Director of the United States Patent and Trademark Office*